(12) United States Patent
Zhou et al.

(10) Patent No.: US 11,484,679 B2
(45) Date of Patent: Nov. 1, 2022

(54) RESPIRATORY MASK CONNECTOR AND RESPIRATORY MASK

(71) Applicant: BMC MEDICAL CO., LTD., Beijing (CN)

(72) Inventors: Mingzhao Zhou, Beijing (CN); Yajie Wang, Beijing (CN); Zhi Zhuang, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 484 days.

(21) Appl. No.: 16/475,949

(22) PCT Filed: Dec. 14, 2017

(86) PCT No.: PCT/CN2017/116047
§ 371 (c)(1),
(2) Date: Jul. 3, 2019

(87) PCT Pub. No.: WO2018/126863
PCT Pub. Date: Jul. 12, 2018

(65) Prior Publication Data
US 2019/0351174 A1 Nov. 21, 2019

(30) Foreign Application Priority Data
Jan. 6, 2017 (CN) .......................... 201710010782.0

(51) Int. Cl.
*A61M 16/06* (2006.01)
*A61M 16/08* (2006.01)

(52) U.S. Cl.
CPC ........ *A61M 16/0825* (2014.02); *A61M 16/06* (2013.01); *A61M 16/0875* (2013.01); *A61M 2205/0216* (2013.01)

(58) Field of Classification Search
CPC .......... A61M 16/0066; A61M 16/0465; A61M 16/0497; A61M 16/06; A61M 16/0611;
(Continued)

(56) References Cited

U.S. PATENT DOCUMENTS 7,188,869 B2 * 3/2007 Garraffa .............. B63C 11/2227
128/202.27
10,828,454 B2 * 11/2020 Harwood .............. A61M 16/06
(Continued)

FOREIGN PATENT DOCUMENTS

CN 103143097 A 6/2013
CN 103764213 A 4/2014
(Continued)

*Primary Examiner* — Annette Dixon
(74) *Attorney, Agent, or Firm* — Volpe Koenig (57) ABSTRACT

A respiratory mask connector and a respiratory mask. The respiratory mask connector is configured to connect a frame to a connection pipe. The respiratory mask connector has a connection face and a spherical face, the connection face being configured to be connected to the frame, and the spherical face being configured to be in ball-socket connection with a pipe head of the connection pipe. The connection face and the spherical face are respectively configured as either the outer wall surface of the respiratory mask connector or the inner wall surface of the respiratory mask connector. The respiratory mask connector can be used for a respiratory mask.

9 Claims, 6 Drawing Sheets

(58) Field of Classification Search
CPC .......... A61M 16/0616; A61M 16/0622; A61M 16/0633; A61M 16/0644; A61M 16/0655; A61M 16/0666; A61M 16/0683; A61M 16/08; A61M 16/0816; A61M 16/0825; A61M 16/0858; A61M 16/0875; A61M 2016/0661; A61M 2039/1033; A61M 2202/0085; A61M 2202/0225; A61M 2205/0216; A61M 2205/42; A61M 2207/00; A61M 2210/0618; A61M 2240/00; A61M 39/10; A61M 39/1055; A62B 18/006; B29C 65/08; B29C 65/62; B29C 66/1122; B29C 66/12881; B29C 66/14; B29C 66/244; B29C 66/2442; B29C 66/43; B29C 66/723; B29L 2031/4835; B63C 11/2227; F16L 27/04; F16L 27/06; Y10T 403/32

See application file for complete search history.

(56) References Cited

U.S. PATENT DOCUMENTS

| | | | | |
|---|---|---|---|---|
| 2003/0200970 A1* | 10/2003 | Stenzler | ............ | A61M 16/0825 128/207.18 |
| 2005/0150497 A1* | 7/2005 | Eifler | ................ | A61M 16/06 128/206.21 |
| 2005/0155603 A1* | 7/2005 | Frerichs | ............ | A61M 16/0633 128/206.21 |
| 2007/0163600 A1* | 7/2007 | Hoffman | ............ | A61M 16/0683 128/207.18 |
| 2007/0209663 A1* | 9/2007 | Marque | ............. | A61M 16/0683 128/207.11 |
| 2010/0229866 A1 | 9/2010 | Sullivan | | |
| 2011/0232649 A1 | 9/2011 | Collazo et al. | | |
| 2012/0138061 A1* | 6/2012 | Dravitzki | .......... | A61M 16/0633 128/205.25 |
| 2016/0067442 A1* | 3/2016 | Salmon | ............. | A61M 16/0683 128/205.25 |
| 2017/0028155 A1* | 2/2017 | Bateman | ........... | A61M 16/0497 |
| 2018/0250485 A1 | 9/2018 | Zhan et al. | | |
| 2018/0256844 A1* | 9/2018 | Galgali | ............. | A61M 16/0605 |
| 2019/0001094 A1 | 1/2019 | Liu et al. | | |
| 2021/0244905 A1* | 8/2021 | Galgali | ................. | A61M 16/06 |

FOREIGN PATENT DOCUMENTS

| | | |
|---|---|---|
| CN | 204193249 U | 3/2015 |
| CN | 104487122 A | 4/2015 |
| CN | 105413036 A | 3/2016 |
| CN | 104906676 A | 9/2016 |
| CN | 106861002 A | 6/2017 |
| DE | 29723101 U1 | 5/1998 |
| WO | 2013006899 A1 | 1/2013 |
| WO | 2013170290 A1 | 11/2013 |

* cited by examiner

RESPIRATORY MASK CONNECTOR AND RESPIRATORY MASK

CROSS REFERENCE TO RELATED APPLICATIONS

The present application claims for the priority of the Chinese Patent Application No. 201710010782.0 filed on Jan. 6, 2017, the entire content of which is incorporated here by reference.

FIELD OF THE INVENTION

The present invention relates to the field of respiratory masks, particularly to a respiratory mask connector for connecting a connection pipe with a frame, and a respiratory mask.

BACKGROUND OF THE INVENTION

Non-intrusive positive pressure ventilation is widely used in the treatment of respiratory problems such as obstructive sleep apnea (OSA), chronic obstructive pulmonary disease (COPD), upper airway resistance syndrome (UARS) and congestive heart failure, etc. Such a treatment approach utilizes a fan to provide continuous positive airway pressure (CPAP) or varying positive airway pressure to the patient through a tube line, instead of inserting a tube into the airway of the patient through a surgical operation.

The existing non-intrusive ventilation treatment process usually requires a respiratory mask. Respiratory masks may be categorized into nasal masks, oral-nasal masks, nasal cushion masks and facial masks, etc.

The typical structure of a respiratory mask comprises a frame, a cushion, a connection pipe, and a head band, etc. The cushion is fixed on the frame, and the cushion and the frame form a gas chamber; the connection pipe is connected with the frame to convey gas to the gas chamber; the head band is connected to the user's head to fix the respiratory mask on the user's head at an appropriate position.

In use, the cushion contacts with the user's face and achieves sealing against the face, and the user's mouth and/or nose are located in the gas chamber.

Owing to the fact that the user always moves his body or head when wearing the respiratory mask, the connection pipe may pull the frame of the respiratory mask, resulting in a poor sealing effect of the cushion and discomfort of the user.

Figure 1:
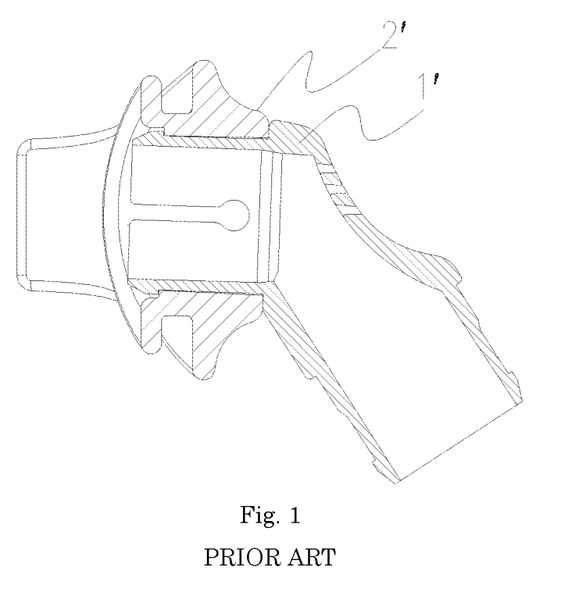
FIG. 1 is a schematic structural diagram of a respiratory mask connector in the prior art.
Figure 2:
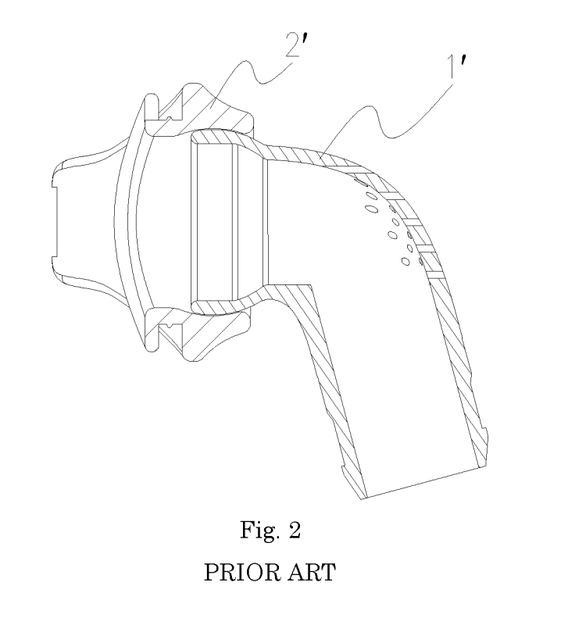
FIG. 2 is a schematic structural diagram of another respiratory mask connector in the prior art.

In order to avoid or reduce the pulling of the connection pipe on the frame, the connection pipe and the frame are usually connected in a way that they can rotate with respect to each other in the prior art. FIGS. 1 and 2 show two types of connection structures between the connection pipe and the frame in the prior art.

The connection structure between the connection pipe and the frame shown in FIG. 1 enables the connection pipe 1' and the frame 2' to rotate with respect to each other within a range of 360 degrees in a plane, but such a connection structure has low degree of freedom of rotation, and attains a limited effect on reducing the pulling of the connection pipe 1' on the frame 2'.

In FIG. 2, the connection pipe 1' and the frame 2' are connected by means of a ball-socket connection. Such a connection structure has higher degree of freedom of rotation, but on one hand, the connection pipe 1' may get loose easily if the opening of the connection between the frame 2' and the connection pipe 1' is too large; on the other hand, it is difficult to mold the rigid frame 2' if the opening of the connection between the frame 2' and the connection pipe 1' is too small.

Therefore, it is desirable to improve the connection structure between the connection pipe and the frame in the prior art, in order to solve at least one problem in the prior art.

SUMMARY OF THE INVENTION

To overcome the drawbacks in the prior art, the present invention provides a novel respiratory mask connector for connecting the connection pipe with the frame of a respiratory mask, and a respiratory mask including the respiratory mask connector.

To attain the object described above, according to a first aspect of the present invention, the present invention provides a respiratory mask connector for connecting a frame with a connection pipe. The respiratory mask connector has a connection face and a spherical face, wherein:

the connection face is configured to be connected with the frame;

the spherical face is configured to be connected with a pipe head of the connection pipe through a ball-socket connection;

wherein, the connection face is one of the outer wall surface and inner wall surface of the respiratory mask connector, and the spherical face is the other of the outer wall surface and inner wall surface of the respiratory mask connector.

Preferably, the outer wall surface is fixedly connected with the frame, and the pipe head is connected with the inner wall surface through a ball-socket connection.

Preferably, the respiratory mask connector is disposed between the frame and the pipe head to separate the frame and the pipe head from each other.

Preferably, the frame has a frame spherical surface, and the pipe head is ball-socket fitted with the spherical face and the frame spherical surface.

Preferably, the respiratory mask connector is an elastic member.

Preferably, the respiratory mask connector is a thin-wall member in thickness of 0.7 mm-1.2 mm.

Preferably, the respiratory mask connector comprises a first connection portion and a second connection portion, wherein:

the first connection portion is configured to be fixedly connected with the frame;

the second connection portion is configured to be fixedly connected with a cushion of the respiratory mask.

Preferably, an open end of the respiratory mask connector oriented to the pipe head is flush with an open end of the frame oriented to the pipe head.

Preferably, the axial length of the pipe head is greater than half of the axial length of the respiratory mask connector.

Preferably, the rigidity of the frame is higher than the rigidity of the respiratory mask connector.

According to a second aspect of the present invention, the present invention provides a respiratory mask, which comprises a connection pipe, a frame, a cushion, and the respiratory mask connector according to the present invention.

In the present invention, the connection face of the respiratory mask connector is connected with the frame, and the spherical face of the respiratory mask connector is connected with the pipe head through a ball-socket connection, so that the connection pipe can rotate with respect to the frame in several degrees of freedom. In addition, through the installation of the respiratory mask connector, the connection pipe is easy to install and can be effectively prevented from getting loose, and the problem that the frame is difficult to mold owing to the direct ball-socket connection between the frame and the connection pipe can be solved.

The respiratory mask connector in the present invention is simple in structure and convenient to assemble, involves low cost, and can be produced in mass production. Other features and advantages of the present invention will become clear through reading the following detailed description of the embodiments of the present invention with reference to the accompanying drawings.

BRIEF DESCRIPTION OF DRAWINGS

The accompanying drawings, which are incorporated in the specification and constitute a part of the specification, illustrate the embodiments of the present invention, and are used in conjunction with their description to explain the principles of the present invention.

IN THE FIGURES

1—connection pipe; 11—pipe head; 2—frame; 21—frame spherical surface; 3—respiratory mask connector; 31—connection face; 32—spherical face; 33—first connection portion; 34—second connection portion; 35—fitting annular groove; 4—cushion; 41—fitting annular protrusion; 5—gas chamber.

DETAILED DESCRIPTION OF THE EMBODIMENTS

Hereunder some embodiments of the present invention will be detailed with reference to the accompanying drawings. It should be noted: unless otherwise specified, the relative arrangements, numerical expressions and values of the components and steps described in those embodiments don't constitute any limitation to the scope of the present invention.

In fact, the following description of at least one embodiment is only illustrative, and shall not be deemed as any limitation to the application or use of the present invention.

Techniques, methods and apparatuses known to those having ordinary skills in the art may not be discussed in detail, but, where appropriate, those techniques, methods and apparatuses shall be considered as a part of the specification.

In all embodiments shown and discussed here, any specific value shall be interpreted as being exemplary rather than limitative. Therefore, different values may be possible in other embodiments.

It should be noted that similar numbers and letters represent similar items in the following drawings. Therefore, once an item is defined in one of the drawings, it is not necessary to discuss it further in the follow-up drawings.

In order to solve the problems existing in the connection structure between the connection pipe and the frame of a respiratory mask in the prior art, the invention provides a respiratory mask connector 3, which, as shown in FIGS. 3-7, is configured to connect a frame 2 with a connection pipe 1.

Figure 3:
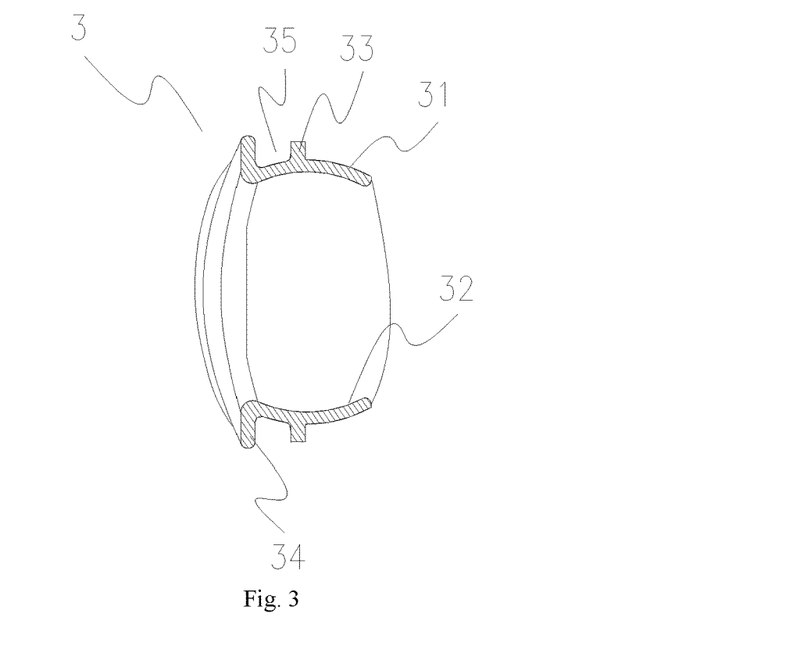
FIG. 3 is a schematic structural diagram of an embodiment of the respiratory mask connector in the present invention.

The respiratory mask connector 3 has a connection face 31 and a spherical face 32.

The connection face 31 is configured to be connected with the frame 2. The connection between the connection face 31 and the frame 2 may be implemented in different ways. For example, the connection between the connection face 31 and the frame 2 may be a fixed connection or detachable connection.

Preferably, the respiratory mask connector 3 and the frame 2 may be connected together by means of protrusion-groove fitting, gluing, or ultrasonic bonding, etc.

The spherical face 32 is configured to be connected with a pipe head 11 of the connection pipe 1 through a ball-socket connection. Those skilled in the art can easily conceive that lubricating oil or lubricating liquid attaining a lubrication effect may be filled between the respiratory mask connector 3 and the pipe head 11.

Wherein, the connection face 31 is one of the outer wall surface and inner wall surface of the respiratory mask connector 3, and the spherical face 32 is the other of the outer wall surface and inner wall surface of the respiratory mask connector 3.

Figure 4:
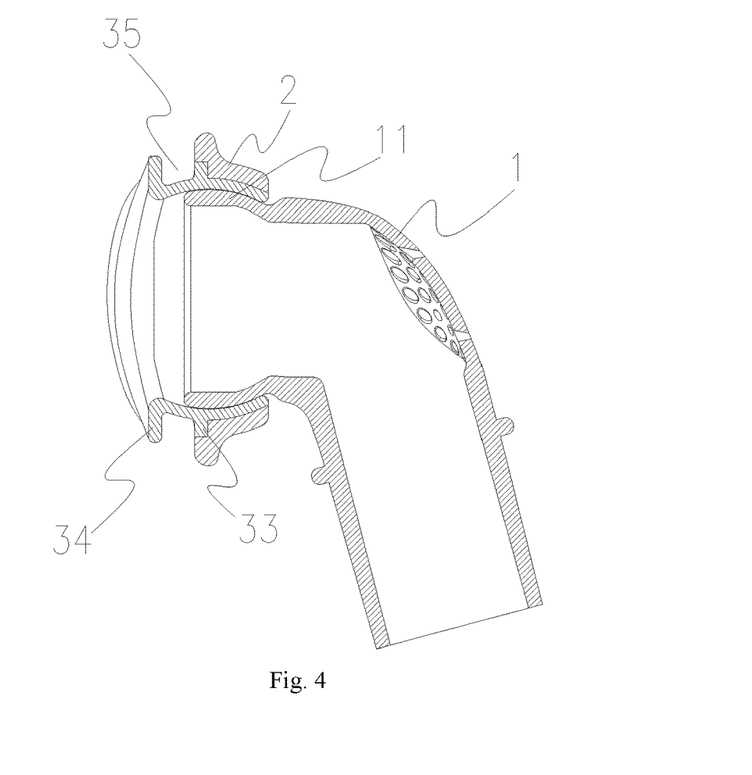
FIG. 4 is a schematic structural diagram of an embodiment of the respiratory mask connector assembled with the frame and the connection pipe in the present invention.
Figure 7:
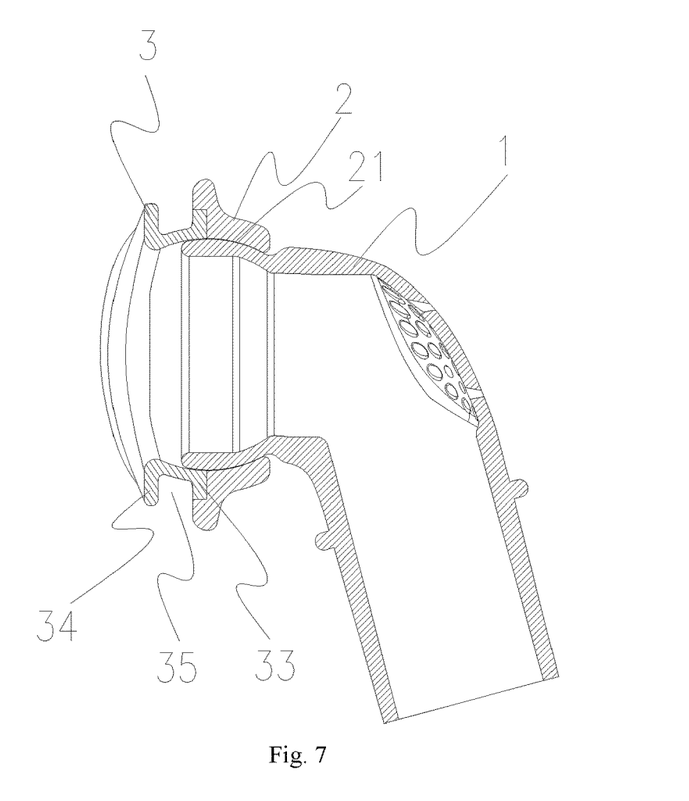
FIG. 7 is a schematic structural diagram of another embodiment of the respiratory mask connector assembled with the frame and the connection pipe in the present invention.

As shown in FIGS. 4 and 7, in a specific embodiment, the connection face 31 may be the outer wall surface of the respiratory mask connector 3, while the spherical face 32 may be the inner wall surface of the respiratory mask connector 3. The outer wall surface of the respiratory mask connector 3 may be connected with the inner surface of the frame 2, while the inner wall surface of the respiratory mask connector 3 may be ball-socket fitted with the outer surface of the pipe head 11. In that way, when the connection pipe 1 and the frame 2 of the respiratory mask are connected, the components arranged sequentially from inside to outside are the pipe head 11, the respiratory mask connector 3, and the frame 2.

Alternatively, the connection face 31 may be the inner wall surface of the respiratory mask connector 3, while the spherical face 32 may be the outer wall surface of the respiratory mask connector 3. The inner wall surface of the respiratory mask connector 3 may be connected with the outer surface of the frame 2, while the outer wall surface of the respiratory mask connector 3 may be ball-socket fitted with the inner surface of the pipe head 11. In that way, when the connection pipe 1 and the frame 2 of the respiratory mask are connected, the components arranged sequentially from inside to outside are the frame 2, the respiratory mask connector 3, and the pipe head 11.

Those skilled in the art may select the specific relation of arrangement among the pipe head 11, the frame 2, and the respiratory mask connector 3 according to the actual requirement.

In the present invention, the connection face 31 of the respiratory mask connector 3 is connected with the frame 2, and the spherical face 32 is connected with the pipe head 11 through a ball-socket connection, so that the connection pipe 1 can rotate with respect to the frame 2 in several degrees of freedom. In addition, through the installation of the respiratory mask connector 3, the connection pipe 1 is easy to install and can be effectively prevented from getting loose, and the problem that the frame 2 is difficult to mold owing to the direct ball-socket connection between the frame 2 and the connection pipe 1 can be solved.

The respiratory mask connector 3 in the present invention is simple in structure and convenient to assemble, involves low cost, and can be produced in mass production.

As shown in FIG. 4, in an embodiment of the respiratory mask connector 3 in the present invention, the outer wall surface of the respiratory mask connector 3 is fixedly connected with the frame 2, and the pipe head 11 is connected with the inner wall surface of the respiratory mask connector 3 through a ball-socket connection. That is to say, the connection face 31 is fixedly connected with the frame 2, and the pipe head 11 and the spherical face 32 are ball-socket fitted with each other.

The fixed connection between the connection face 31 and the frame 2 may be implemented by means of one or more of protrusion-groove fitting, gluing, and ultrasonic bonding, etc.

In the above embodiment, the respiratory mask connector 3 may be assembled with the connection pipe 1 and the frame 2 more conveniently.

Figure 5:
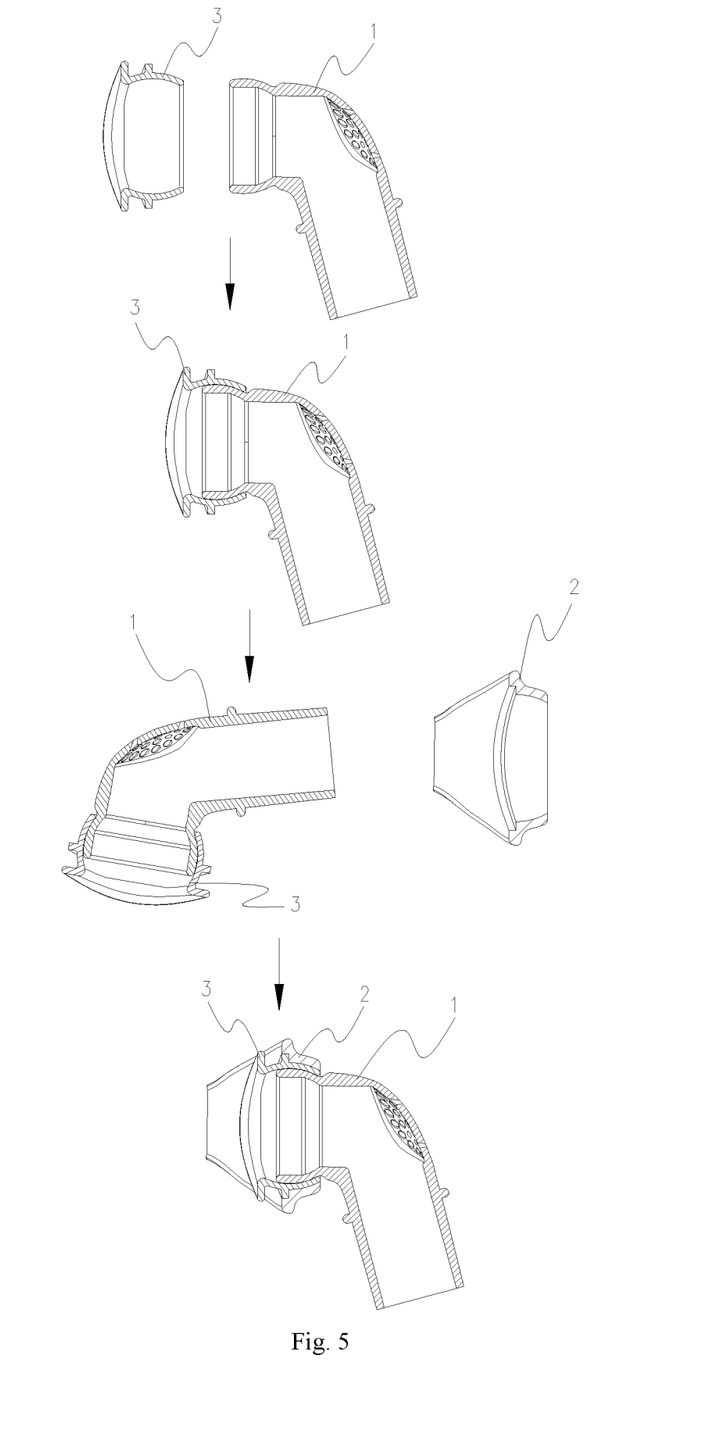
FIG. 5 is a schematic diagram of the assembling process of the respiratory mask connector, frame, and connection pipe in FIG. 4.

For example, in the assembling process of the respiratory mask connector 3, frame 2, and connection pipe 1 shown in FIG. 5, first, the pipe head 11 of the connection pipe 1 may be assembled to the respiratory mask connector 3; then the connection pipe 1 and the respiratory mask connector 3 that are assembled together may be assembled in the frame 2; next, the respiratory mask connector 3 and the frame 2 may be connected together, for example, by ultrasonic bonding. In that way, the frame 2 encloses the connection face 31 of the respiratory mask connector 3, and thereby the respiratory mask connector 3 is not easy to deform, and the connection pipe 1 is not easy to get loose.

FIG. 4 is a schematic structural diagram of an embodiment of the respiratory mask connector 3 assembled with the frame 2 and the connection pipe 1 in the present invention. In FIG. 4, the respiratory mask connector 3 is disposed between the frame 2 and the pipe head 11, so as to separate the frame 2 and the pipe head 11 from each other. Thus, the respiratory mask connector 3 completely separates the frame 2 from the pipe head 11, so that the pipe head 11 can rotate with respect to the respiratory mask connector 3 smoothly, and any rotation retardation can be avoided.

Figure 10:
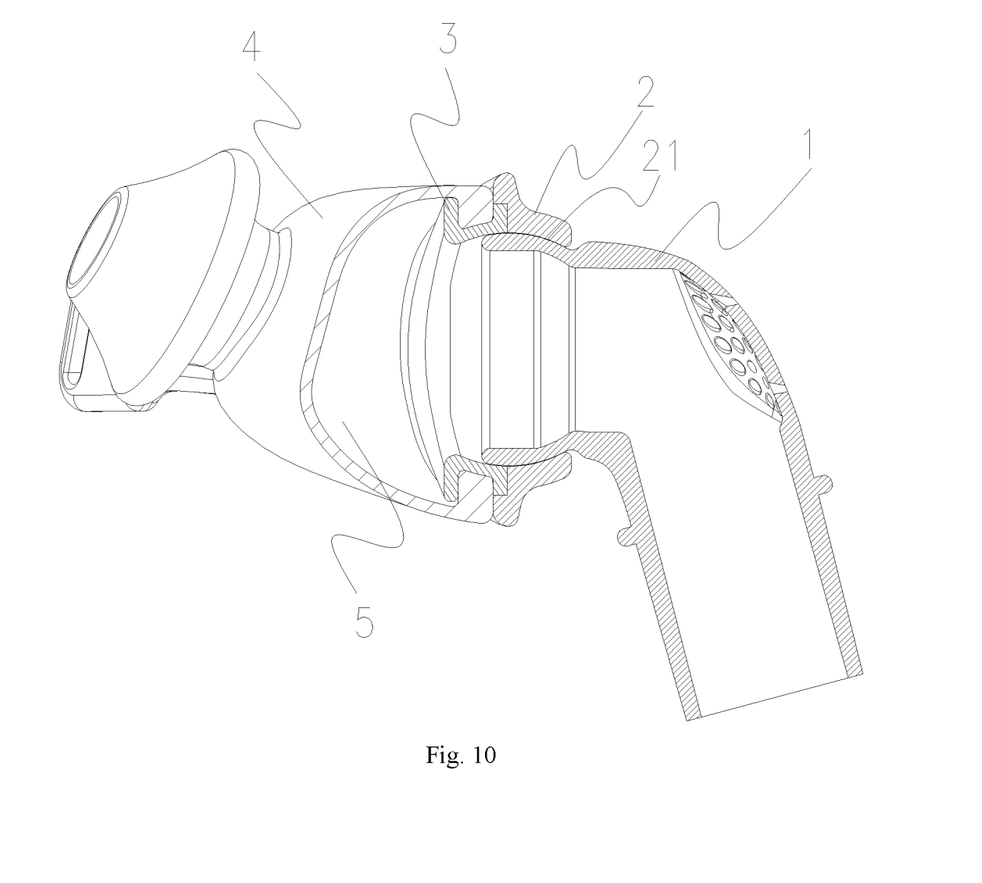
FIG. 10 is a schematic structural diagram of another embodiment of the respiratory mask in the present invention.

FIG. 7 is a schematic structural diagram of another embodiment of the respiratory mask connector 3 assembled with the frame 2 and the connection pipe 1 in the present invention. In FIGS. 7 and 10, the frame 2 has a frame spherical surface 21, and the pipe head 11 is ball-socket fitted with the spherical face 32 and the frame spherical surface 21. In that way, the pipe head 11 of the connection pipe 1 is ball-socket fitted with the spherical face 32 of the respiratory mask connector 3 and the frame spherical surface 21 of the frame 2 at the same time, so that the reliability of the ball-socket fitting of the pipe head 11 is improved.

Smooth transition may be arranged between the spherical face 32 and the frame spherical surface 21, so that the spherical face 32 and the frame spherical surface 21 form a part of a spherical face.

Optionally, the respiratory mask connector 3 is an elastic member, so that the respiratory mask connector 3 can be assembled with the connection pipe 1 and the frame 2 more conveniently.

In a specific embodiment, the respiratory mask connector 3 may be a thin-wall member, so as to improve the elastic deformation ability of the respiratory mask connector 3. More specifically, the wall thickness of the thin-wall member preferably is 0.7 mm-1.2 mm.

In another embodiment of the respiratory mask connector 3 in the present invention, the respiratory mask connector 3 comprises a first connection portion 33 and a second connection portion 34. The first connection portion 33 is configured to be fixedly connected with the frame 2. The second connection portion 34 is configured to be fixedly connected with a cushion 4 in the respiratory mask.

In a specific embodiment, both the first connection portion 33 and the second connection portion 34 may be on the connection face 31 of the respiratory mask connector 3. Alternatively, both the first connection portion 33 and the second connection portion 34 may be on the outer wall surface of the respiratory mask connector 3.

Preferably, as shown in FIGS. 4 and 7, the first connection portion 33 is a protrusion that extends outward from the connection face 31 of the respiratory mask connector 3, and the frame 2 is arranged with a groove that is intended to be fitted with the protrusion. The protrusion and the groove may be connected with each other by engagement. Alternatively, based on the engagement between the protrusion and the groove, the contact surfaces of the protrusion and the groove are further connected by gluing and/or ultrasonic bonding, to ensure the reliability of the connection between the respiratory mask connector 3 and the frame 2.

Figure 6:
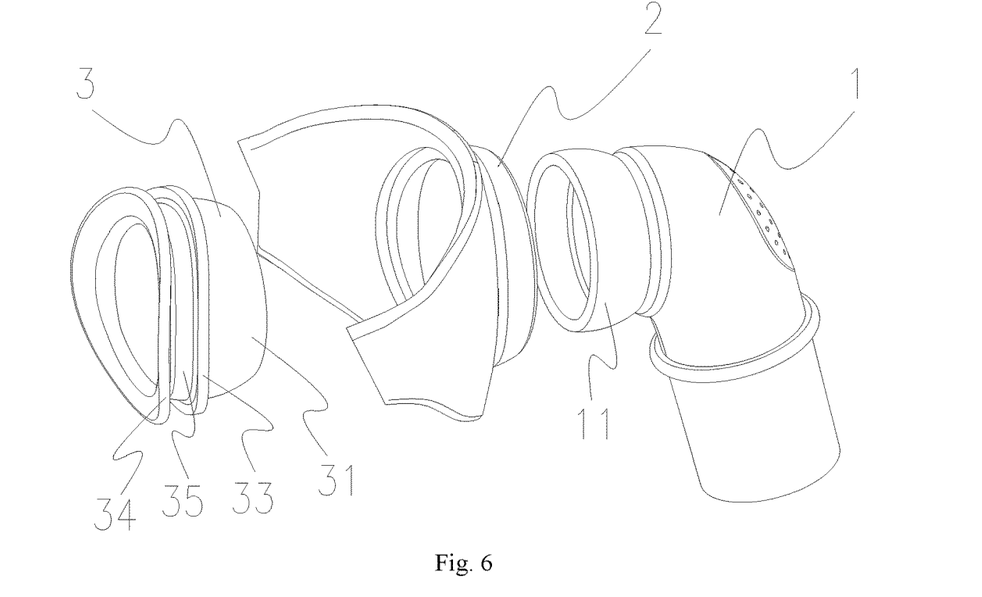
FIG. 6 is an exploded view of the structure in FIG. 4.
Figure 9:
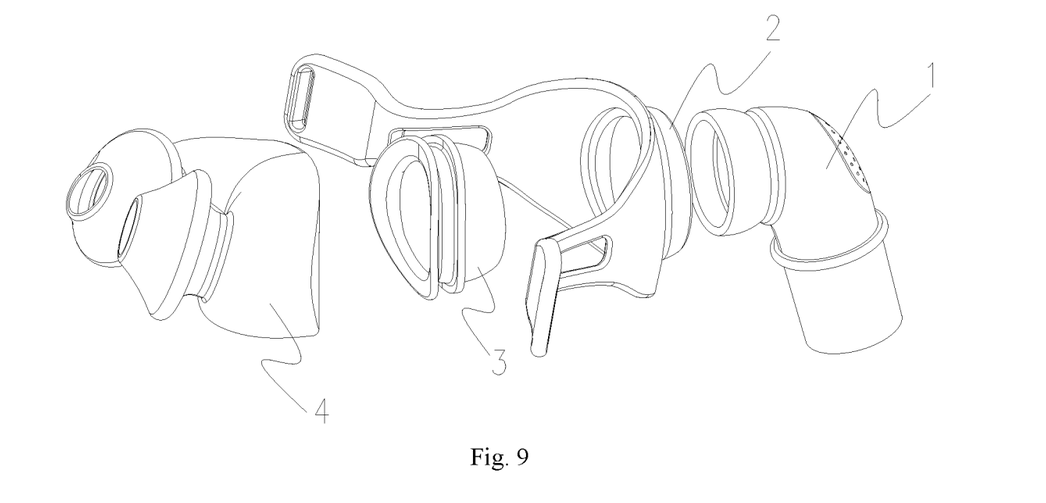
FIG. 9 is an exploded view of the structure in FIG. 8.

As shown in FIGS. 6 and 9, the first connection portion 33 may be an annular protrusion. The specific quantity of the protrusions may be selected flexibly according to the actual requirement. For example, the respiratory mask connector 3 may have one annular protrusion serving as the first connection portion 33; alternatively, the respiratory mask connector 3 may be provided with a plurality of annular protrusions arranged to be parallel or not parallel to each other as the first connection portion 33.

As shown in FIGS. 6 and 9, the second connection portion 34 may be an annular protrusion. The specific quantity of the protrusions may be selected flexibly according to the actual requirement. For example, the respiratory mask connector 3 may have one annular protrusion serving as the second connection portion 34; alternatively, the respiratory mask connector 3 may be provided with a plurality of annular protrusions arranged to be parallel or not parallel to each other as the second connection portion 34. Here, a groove intended to be fitted with the second connection portion 34 may be arranged in the cushion 4. The protrusion and the groove may be connected with each other by engagement. Alternatively, based on the engagement between the protrusion and the groove, the contact surfaces of the protrusion and the groove are further connected by gluing and/or ultrasonic bonding, to ensure the reliability of the connection between the respiratory mask connector 3 and the cushion 4.

As shown in FIGS. 4, 7, and 8-10, in a specific embodiment, both the first connection portion 33 and the second connection portion 34 are protrusions extending outward from the connection face 31 of the respiratory mask connector 3, and a fitting annular groove 35 is formed between the first connection portion 33 and the second connection portion 34. A fitting annular protrusion 41 intended to be fitted with the fitting annular groove 35 is arranged in the cushion 4. The fitting annular protrusion 41 and the fitting annular groove 35 may be connected together by engagement. Alternatively, based on the engagement between the fitting annular protrusion 41 and the fitting annular groove 35, the contact surfaces of the fitting annular protrusion 41 and the fitting annular groove 35 are further connected by gluing and/or ultrasonic bonding, to ensure the reliability of the connection between the respiratory mask connector 3 and the cushion 4.

Of course, the first connection portion and the second connection portion are not limited to the protrusions on the connection face 31; instead, the first connection portion may be the entire connection face 31 or a part of the connection face 31. Optionally, the first connection portion is the entire connection face 31, in order to ensure the reliability of the connection between the respiratory mask connector 3 and the frame 2.

The second connection portion may be a fitting annular groove 35, and the cushion 4 may be directly connected with the fitting annular groove 35 to realize the connection between the respiratory mask connector 3 and the cushion 4. The first connection portion and the second connection portion are not limited to the specific embodiments described above, as long as the first connection portion can ensure the reliability of the connection between the respiratory mask connector 3 and the frame 2, and the second connection portion can ensure the reliability of the connection between the respiratory mask connector 3 and the cushion 4.

In another embodiment of the respiratory mask connector 3 in the present invention, the open end of the respiratory mask connector 3 oriented to the pipe head 11 is flush with the open end of the frame 3 oriented to the pipe head 11. For example, as shown in FIG. 4, the right port of the respiratory mask connector 3 is flush with the right port of the frame 2. The arrangement that the open end of the respiratory mask connector 3 oriented to the pipe head 11 is flush with the open end of the frame 2 oriented to the pipe head 11 is helpful for ensuring smooth rotation of the connection pipe 1 and improving the aesthetic appearance of the respiratory mask.

To prevent the pipe head 11 from falling out from the respiratory mask connector 3, the axial length of the pipe head 11 is greater than half of the axial length of the respiratory mask connector 3. The arrangement that the length of the pipe head 11 is greater than half of the length of the respiratory mask connector 3 is helpful for improving the smoothness of rotation of the connection pipe 1 inside the respiratory mask connector 3.

In yet another embodiment of the respiratory mask connector 3 in the present invention, the rigidity of the frame 2 is higher than the rigidity of the respiratory mask connector 3. Those skilled in the art know that the rigidity refers to the elastic deformation resisting ability of a material or structure under stress.

The feature that the rigidity of the frame 2 is higher than the rigidity of the respiratory mask connector 3 is helpful for ensuring the enclosing ability of the frame 2 for the respiratory mask connector 3, so that the connection pipe 1 will not get loose easily, the difficulty in molding of the respiratory mask connector 3 is decreased, and the cost of the respiratory mask connector 3 is reduced.

Preferably, in a specific embodiment, the frame 2 is made of a rigid plastic material, while the respiratory mask connector 3 is made of a semi-rigid plastic material. More specifically, the frame 2 may be made of polycarbonate (PC), acrylonitrile butadiene styrene copolymer (ABS) or nylon (polyamide), etc..; the respiratory mask connector 3 may be made of polypropylene (PP), polyethylene (PE), polyamide 66 or nylon 66 (PA66), or thermoplastic elastomer (TPE), etc.

Figure 8:
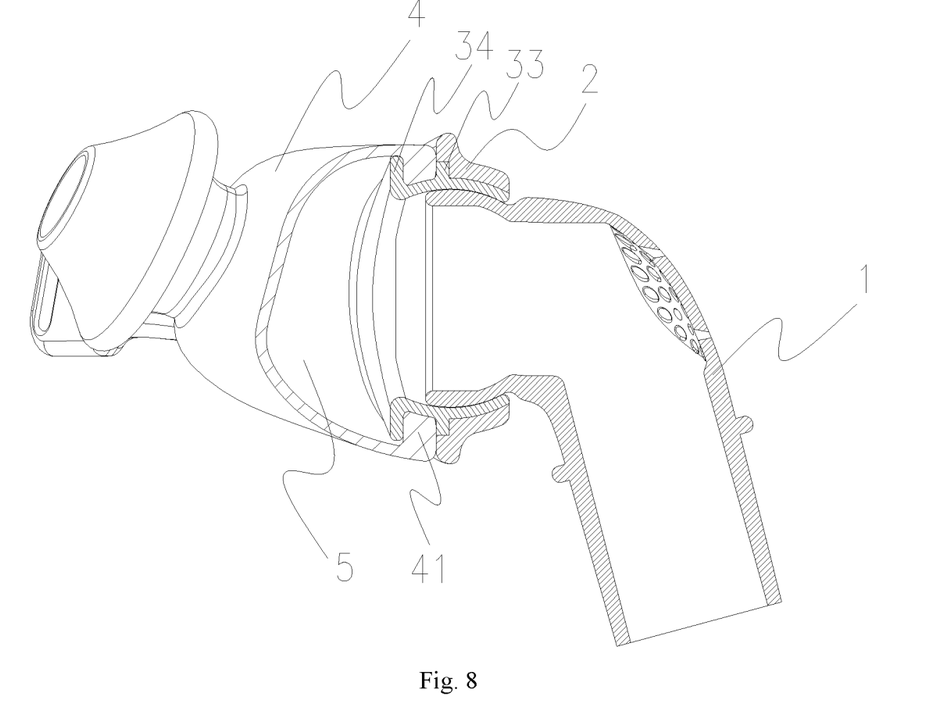
FIG. 8 is a schematic structural diagram of an embodiment of the respiratory mask in the present invention.

As shown in FIGS. 8-10, the present invention further provides a respiratory mask. The respiratory mask comprises a connection pipe 1, a frame 2, a cushion 4, and the respiratory mask connector 3 according to the present invention.

As shown in FIG. 8, in an embodiment of the respiratory mask in the present invention, the inner wall surface (a spherical face 32) of the respiratory mask connector 3 is ball-socket fitted with a pipe head 11 of the connection pipe 1. The outer wall surface (a connection face 31) of the respiratory mask connector 3 is arranged with a first connection portion 33 and a second connection portion 34, both of which are annular protrusions. A fitting annular groove 35 is formed between the first connection portion 33 and the second connection portion 34. A fitting annular protrusion 41 intended to be fitted with the fitting annular groove 35 is arranged in the cushion 4.

To assemble the respiratory mask in the present invention, first, the pipe head 11 of the connection pipe 1 may be assembled to the respiratory mask connector 3; then, the connection pipe 1 and the respiratory mask connector 3 that are assembled together may be assembled in the frame 2. Thus, the connection face 31 of the connecting member 3 is enclosed by the frame 2, and the opening of the connecting member 3 is not easy to deform. Therefore, the connection pipe 1 will not get loose easily. Next, the respiratory mask connector 3 and the frame 2 may be connected together, for example, by ultrasonic bonding; then the cushion 4 may be assembled to the respiratory mask connector 3.

When the respiratory mask in the present invention is used, the cushion 4 contacts with the face of the user and achieves sealing against the face of the user, the mouth and/or nose of the user is located in the gas chamber 5, and the connection pipe 1 conveys gas to the gas chamber 5 for the user to breathe.

When the user wearing the respiratory mask moves his/her body or head, the connection pipe 1 will rotate inside the respiratory mask connector 3 with respect to the frame 2, and thereby the pulling of the connection pipe 1 on the frame 2 is reduced or avoided, the sealing effect of the cushion 4 is ensured, and the wearing comfortability of the user is improved.

Although some particular embodiments of the present invention have been described in detail above in examples, those skilled in the art should appreciate that the above examples are provided only for the purpose of description rather than limiting the scope of the present invention. Those skilled in the art should appreciate that various modifications can be made to the above embodiments without departing from the scope and spirit of the present invention. The scope of the present invention is only defined by the appended claims.

The invention claimed is:

1. A respiratory mask connector for connecting a frame with a connection pipe, having a connection face and a spherical face, wherein:
   the connection face is configured to be connected with the frame;

the spherical face is configured to be connected with a pipe head of the connection pipe through a ball-socket connection, wherein, the connection face is the outer wall surface of the respiratory mask connector, and the spherical face is the inner wall surface of the respiratory mask connector; wherein the respiratory mask connector is circumferentially clamped between the frame and the pipe head to separate the frame and the pipe head from each other; and the respiratory mask connector is a one-piece elastic member, and the rigidity of the frame is higher than the rigidity of the respiratory mask connector.

2. The respiratory mask connector of claim 1, wherein, the outer wall surface is fixedly connected with the frame, and the pipe head is connected with the inner wall surface through a ball-socket connection.

3. The respiratory mask connector of claim 2, wherein, the axial length of the pipe head is greater than half of the axial length of the respiratory mask connector.

4. The respiratory mask connector of claim 1, wherein, the respiratory mask connector is a thin-wall member in thickness of 0.7 mm-1.2 mm.

5. The respiratory mask connector of claim 1, wherein, an open end of the respiratory mask connector oriented to the pipe head is flush with an open end of the frame oriented to the pipe head.

6. A respiratory mask, comprising a connection pipe, a frame, a cushion, and the respiratory mask connector of claim 1.

7. The respiratory mask connector of claim 1 comprising a first connection portion and a second connection portion, wherein, the first connection portion is configured to be fixedly connected with the frame; the second connection portion is configured to be fixedly connected with a cushion of a respiratory mask.

8. A respiratory mask connecting assembly, comprising a frame and a respiratory mask connector, the respiratory mask connector is configured to connect the frame to a connection pipe, the respiratory mask connector having a connection face and a spherical face, wherein:

the connection face is connected with the frame;

the spherical face is configured to be connected with a pipe head of the connection pipe through a ball-socket connection, wherein, the connection face is the outer wall surface of the respiratory mask connector, and the spherical face is the inner wall surface of the respiratory mask connector; wherein the respiratory mask connector is circumferentially clamped between the frame and the pipe head to separate the frame and the pipe head from each other; and wherein the respiratory mask connector is a one-piece elastic member, and the rigidity of the frame is higher than the rigidity of the respiratory mask connector.

9. The respiratory mask connecting assembly of claim 8, wherein, the outer wall surface is fixedly connected with the frame, and the pipe head is connected with the inner wall surface through a ball-socket connection.

\* \* \* \* \*